United States Patent [19]
Connor et al.

[11] Patent Number: 5,612,330
[45] Date of Patent: Mar. 18, 1997

[54] METHODS FOR INHIBITING AND CONTROLLING VIRAL GROWTH

[75] Inventors: David T. Connor; Stephen J. Gracheck, both of Ann Arbor, Mich.

[73] Assignee: Warner-Lambert Company, Morris Plains, N.J.

[21] Appl. No.: 408,431

[22] Filed: Mar. 22, 1995

Related U.S. Application Data

[63] Continuation-in-part of Ser. No. 351,611, Dec. 12, 1994, Pat. No. 5,489,586, which is a continuation-in-part of Ser. No. 207,330, Mar. 7, 1994, abandoned.

[51] Int. Cl.$^6$ .......................... A61K 31/55; C07D 513/04
[52] U.S. Cl. ........................... 514/211; 514/220; 540/495
[58] Field of Search ........................................ 514/211, 220

[56] References Cited

U.S. PATENT DOCUMENTS 4,013,641   3/1977   Brown ..................................... 260/239

FOREIGN PATENT DOCUMENTS 9417075   8/1994   WIPO ..................................... 340/489

OTHER PUBLICATIONS

M. Hiroaki, et al., *Proc Natl Acad Sci USA*, 83:1986, 1911–15.

B.C. Hakkert, et al., *Blood*, vol. 78, No. 10, 1991, 2721–2726.

J. Pober, et al., *J Immun*, 137, No. 6, 1986, 1893–96.

C. W. Smith, et al., *J Clin Invest*, 82, 1988, 1746–56.

M.P. Bevilacqua, et al., *Proc Natl Acad Sci, USA*, 84, 1987.

M.A. Vadas, *Biochemical Pharm*, 40 (8), 1990, 1683–87.

M.A. Jutila, et al., *Transplantation*, 48, 1989, 727–31.

A. Wardlaw, *Clin & Exper Allergy*, 20, 1990, 619–626.

R.P. McEver, *Thrombosis & Hemostasis*, 65 (3), 1991, 223–228.

T. A. Springer, *Nature*, 346, 1990, 425–434.

PCT Search Report, PCT/US 95/01275.

*Chemical Abstracts*, vol. 105, No. 25, 1986, abstract No. 226266q, Nagarajan et al.

*Chemical Abstracts*, vol. 115, No. 21, 1991, abstract No. 232194n, Hiremath et al.

*Chemical Abstracts*, vol. 89, No. 5, 1978, abstract No. 43178u, Glushkov et al.

*Primary Examiner*—Robert T. Bond
*Attorney, Agent, or Firm*—Charles W. Ashbrook

[57] ABSTRACT

Benzothiophene, benzofuran and indolethiazepinones, oxazepinones, and diazepinones are effective therapeutic agents for treating viral diseases, including those caused by herpesvirus and HIV.

11 Claims, No Drawings

METHODS FOR INHIBITING AND CONTROLLING VIRAL GROWTH

CROSS REFERENCE TO RELATED APPLICATIONS

This is a continuation-in-part of U.S. application Ser. No. 08/351,611 filed Dec. 12, 1994, now U.S. Pat. No. 5,489,586 which is a continuation-in-part of U.S. application Ser. No. 08/207,330 filed Mar. 7, 1994, now abandoned.

FIELD OF THE INVENTION

The present invention discloses a series of benzothiophene, benzofuran and indole-thiazepinones, oxazepinones, and diazepinones which substantially inhibit the human immunodeficiency virus (HIV) and inhibit the activation of HIV in HIV-infected individuals. In addition, the present invention provides methods of using these compounds as immunosuppressives and for the treatment of other diseases of the immune system. The invention provides a method for treating herpes viral infections, including conditions caused by herpes simplex I, such as cold sores, herpes simplex II such as genital herpes, as well as shingles caused by herpes zoster, and infections caused by cytomegalovirus, Epstein-Barr virus, and V2V.

BACKGROUND

The pathogenesis of the human immunodeficiency virus (HIV) is complicated and as of yet not completely understood. The virus life cycle has theoretically been divided into afferent and efferent components. Virus binding, fusion, reverse transcription, and finally integration are among those events which encompass the afferent component of the life cycle. It is the afferent component of the HIV life cycle which is responsible for primary infection of HIV in an individual, generally followed by a burst of viraemia with or without clinical symptoms.

In most individuals, a prolonged clinically asymptomatic period follows infection with the human immunodeficiency virus type 1 (HIV-1). During this period that normally spans 8 to 10 years, infected individuals remain in good health with adequate immune responsiveness. However, in the years that follow, the occurrence of opportunistic infections and the rapid devastation of immune responsiveness that characterizes AIDS eventually result in death. Therefore, the clinically asymptomatic period presents a therapeutic window of opportunity to prevent immune destruction if effective intervention can be implemented.

Key to the development of therapeutic intervention designed to prolong the asymptomatic period prior to AIDS is an understanding of the progressive events that ultimately result in immune destruction. While the influences controlling clinical progression to AIDS are certainly multifactorial, a critical facet is the continued replication of HIV-1 within target cells and tissues, especially the lymph nodes. In addition, there exist a large population of HIV-1 infected cells, in the peripheral circulation and the lymph nodes, that maintain the provirus in a clinically latent state. Based on currently available in vitro models of HIV-1 infection, when these latently infected cells encounter the proper extracellular stimuli, HIV-1 becomes replicationally active and produces progeny virions to further disseminate infection. Therefore, therapeutic intervention to alter clinical progression during the asymptomatic period must not only address the control of active HIV-1 replication, but also the inhibition of viral activation from microbiological latency.

An area that warrants further development is therapeutic targeting along cellular signaling pathways that result in HIV-1 transcriptional activation. Among the potential targets is nuclear factor-κB (NF-κB), a transcriptional enhancer important for HIV-1 activation. In resting cells, preformed NF-κB exists in the cytoplasm bound to its inhibitor I-κB. After immune or cytokine stimulation of the cell, NF-κB is released by phosphorylation, and proteolysis of I-κB, and translocates to the nucleus to activate transcription from promoters, including HIV-1, that contain a specific binding motif. Anti-oxidants and other pharmacologic agents that block HIV-1 promoter-directed gene expression may interfere with NF-κB activation or with other viral enhancers. Selective inhibition of cellular protein kinase C activity has also proven effective against HIV-1 expression. However, targeting of cellular signaling elements must retain some degree of viral specificity, otherwise these therapies may interfere with normal cellular and immune functions.

We have now discovered a series of benzothiophene, benzofuran and indole derivatives which are effective at inhibiting HIV-1 activation. Viral inhibition by these compounds resulted from a specific interference with HIV-1 transcription by targeting a cellular component other than NF-κB. Furthermore, these compounds returned cytokine-activated, HIV-expressing cells to a state of viral latency, even under conditions of continued viral stimulation, and prevented HIV-1 expression during chronic infection. The compounds also inhibit herpes virus, including herpes simplex I and II, and cytomegalovirus. Accordingly, these compounds are useful for treating and preventing cold sores, genital herpes, shingles, and cytomegalovirus retinitis.

An object of this invention is therefore to provide a method for inhibiting HIV or the activation of HIV in an HIV-infected individual, and a method for preventing and treating conditions caused by herpesviruses.

SUMMARY OF THE INVENTION

This invention is a method for inhibiting HIV or the activation of HIV comprising administering to a patient in need of treatment an effective amount of a benzothiophene, benzofuran or indole-thiazepinone, oxazepinone, or diazepinone. The invention more particularly provides a method of treatment comprising administering a compound of Formula I, or a pharmaceutically acceptable salt thereof.

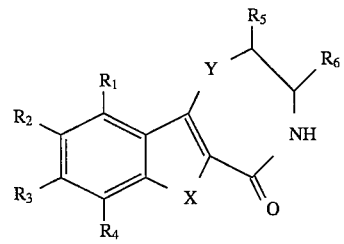

or a pharceutically acceptable acid addition salt thereof, wherein $R_1$, $R_2$, $R_3$, and $R_4$ are each independently hydrogen, hydroxy, halogen, lower alkyl, lower alkoxy, benzyloxy, trifluoromethyl, nitro, or —$NR_8R_9$, in which $R_8$ and $R_9$ are each independently hydrogen or lower alkyl;

$R_5$ and $R_6$ are each independently hydrogen, lower alkyl or phenyl;

X is O, S$(O)_n$ or $NR_7$;

Y is O, $S(O)_n$ or $NR_8$;

$R_7$ is hydrogen, lower alkyl, phenyl, benzyl, $CH_2OR_8$ or lower alkyl, phenyl, benzyl substituted with halo;

$R_8$ is hydrogen, lower alkyl or phenyl;

n is an integer of 0, 1 or 2;

with the provisos that 1) when X is NH, Y is NH, $R_1$ is H, $R_3$ is H and $R_4$ is Br, $R_2$ is not methyl;

2) when X is NH, Y is NH, $R_1$, $R_3$ and $R_4$ are H, $R_2$ is not methoxy or ethoxy; and 3) when X is NH, Y is S, at least one of $R_1$, $R_2$, $R_3$, and $R_4$ is not H.

DETAILED DESCRIPTION

The terms used in defining the compounds of Formula I of the present invention are defined as follows:

Lower alkyl and lower alkoxy mean a straight or branched alkyl or alkoxy group having 1 to 4 carbon atoms and includes, for example, methyl, ethyl, propyl, i-propyl, or otherwise referred to as (methyl)ethyl, and t-butyl or otherwise referred to as 1,1-(dimethyl)ethyl, and correspondingly, for example, methoxy, ethoxy, i-propoxy, or otherwise referred to as 1-(methyl)ethoxy and the like.

Halogen includes fluorine, chlorine, bromine, or iodine.

The compounds of the Formula I are capable of further forming pharmaceutically acceptable acid addition salts. All of these forms are within the scope of the present invention.

Pharmaceutically acceptable acid addition salts of the compounds of Formula I include salts derived from inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenylsubstituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate, N-methyl glutamine (see, for example, Berge S. M., et al., "Pharmaceutical Salts," *Journal of Pharmaceutical Science*, 66:1–19 (1977)).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

A preferred method of the present invention employs a compound of Formula I, wherein $R_1$, $R_3$ and $R_4$ are hydrogen and $R_2$ is as defined above.

A more preferred method of the present invention employs a compound of Formula I, wherein $R_1$, $R_3$ and $R_4$ are hydrogen; $R_2$ is hydrogen or lower alkoxy; X is O, $S(O)_n$ or $NR_7$; Y is O or $S(O)_n$; $R_7$ is hydrogen or lower alkyl, and n is 0, 1, or 2.

Particularly valuable compounds to be utilized in the present method are:

2,3-dihydro-9-methoxy-[1]benzothieno-[2,3-f]-1,4-thiazepin-5(4H)-one, 2,3-dihydro-[1]benzothieno[2,3-f]-1,4-oxazepin-5(4H)-one, 2,3-dihydro-9-methoxy-[1]benzothieno[2,3-f]-1,4-thiazepin-5(4H)-one-1-oxide, 3,4-dihydro-9-methoxy-6-methyl-2H-1,4 -oxazepin-[6,7-b]-indol-5(6H)-one, 2,3-dihydro-1H-benzothieno-[3,2-e]-1,4-diazepine-5-one, 2,3-dihydro-9-methoxy-1H-benzothieno-[2,3-f]-1,4-oxazepine-5-one, 2,3-dihydro-9-methoxy-6-oxide-1H-benzothieno-[2,3-f]oxazepine-5-one, 2,3-dihydro-9-methoxy-2-methyl-1H-benzothieno-[2,3-f]-1,4-oxazepine-5-one, 2,3-dihydro -7,8,9,10-tetrachloro-1H-benzothieno [2,3-f]-1,4-oxazepine-5-one, 3,4-dihydro -8-nitro-6-tert.-butyl-2H-1,4-oxazepine [6,7-b]indol-5(6H)-one, 3,4-dihydro -9-isopropoxy-6-phenoxymethyl-2H-1,4-oxazepine [6,7-b]indol-5(6H)-one hydrochloride, 3,4-dihydro-8,10-dibromo-6-(3-chlorobenzyl-2H-1,4-oxazepino [6,7-b]indol-5(6H)-one, 2,3-dihydro-8-chloro-1H-benzofurano[2,3-f]-1,4-oxazepine-5-one, methanesulfonate, 2,3-dihydro-1,2,3-trimethyl-1H-benzofurano[3,2-e]-1,4-diazepine-5-one, and 2,3-dihydro-3-hexyl-1H-benzofurano[2,3-f]-1,4-thiazepine-5-one.

In determining when an inhibitor of HIV activation is indicated, of course inter alia, the particular condition in question and its severity, as well as the age, sex, weight, and the like of the subject to be treated, must be taken into consideration and this determination is within the skill of the attendant physician.

For medical and veterinary use according to this invention, the amount required of a compound of Formula I or a pharmacologically acceptable acid addition salt thereof to achieve a therapeutic effect will, of course, vary both with the particular compound, the route of administration, the mammal under treatment, and the particular disorder or disease concerned. A suitable dose of a compound of Formula I or a pharmacologically acceptable acid addition salt thereof for a mammal suffering from, or likely to suffer from any condition as described hereinbefore is 0.1 µg to 500 mg of the compound per kilogram body weight. In the case of systemic administration, the dose may be in the range of 0.5 to 500 mg of the compound per kilogram body weight, the most preferred dosage being 0.5 to 50 mg/kg of mammal body weight administered two to three times daily. In the case of topical administration, e.g., to the skin or eye, a suitable dose may be in the range 0.1 ng to 100 µg of the compound per kilogram, typically about 0.1 µg/kg.

In the case of oral dosing for the treatment or prophylaxis of AIDS in general, due to any cause, a suitable dose of a compound of Formula I or a physiologically acceptable acid addition salt thereof, may be as specified in the preceding paragraph, but most preferably is from 1 mg to 10 mg of the compound per kilogram, the most preferred dosage being from 1 mg to 5 mg/kg of mammal body weight, for example, from 1 to 2 mg/kg. The invention compounds can be utilized in combination with other antiviral agents, for example, AZT and acyclovir.

It is understood that the ordinarily skilled physician or veterinarian will readily determine and prescribe the effective amount of the compound to prevent or arrest the progress of the condition for which treatment is administered. In so proceeding, the physician or veterinarian could employ relatively low doses at first, subsequently increasing the dose until a maximum response is obtained.

While it is possible for an active ingredient to be administered alone, it is preferable to present it as a pharmaceutical formulation comprising a compound of Formula I or a pharmacologically acceptable acid addition salt thereof and a pharmacologically acceptable carrier therefor.

The formulations, both for veterinary and for human medical use, comprise an active ingredient in association with a pharmaceutically acceptable carrier therefor and optionally other therapeutic ingredient(s). The carrier(s) must be 'acceptable' in the sense of being compatible with the other ingredients of the formulations and not deleterious to the recipient thereof.

The formulations include those in a form suitable for oral, pulmonary, ophthalmic, rectal, parenteral (including subcutaneous, intramuscular, and intravenous), intraarticular, topical, nasal, or buccal administration. Such formulations are understood to include long-acting formulations known in the art.

The formulations may conveniently be presented in unit dosage form and may be prepared by any of the methods well known in the art of pharmacy. All methods may include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units such as capsules, cachets, tablets, or lozenges, each containing a predetermined amount of the active ingredient; in the form of a powder or granules; in the form of a solution or a suspension in an aqueous liquid or nonaqueous liquid; or in the form of an oil-in-water emulsion or a water-in-oil emulsion. The active ingredient may also be in the form of a bolus, electuary, or paste.

Solid form preparations include powders, tablets, dispersible granules, capsules, cachets, and suppositories. A solid carrier can be one or more substances which may also act as diluents, flavoring agents, solubilizers, lubricants, suspending agents, binders or tablet disintegrating agents; it can also be an encapsulating material. In powders, the carrier is a finely divided solid which is in admixture with the finely divided active compound of Formula I. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, transdermal and transmucosal systems, and capsules can be used as solid dosage forms suitable for oral administration.

Liquid form preparations include solutions, suspensions, and emulsions. As an example, water or water-propylene glycol solutions may be mentioned for parenteral injection. Liquid preparations can also be formulated in solution in aqueous polyethylene glycol solution. Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water with viscous material, i.e., natural or synthetic gums, resins, methyl cellulose, sodium carboxymethyl cellulose and other well-known suspending agents. Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these in packaged form.

The compounds of the present invention have been found to inhibit the activation of the human immunodeficiency virus (HIV), latent in infected mammals, and therefore are useful in the treatment of AIDS.

Attempts at understanding the virologic and cellular basis for the clinical asymptomatic period reveal that HIV exists as a dormant or nonexpressing provirus in a reservoir population of chronically infected cells. A specific type of HIV, HIV-1, has been the subject of a number of different research projects which have shown that the virus exists as a dormant or nonexpressing provirus in a reservoir population of chronically infected T-lymphocytic cells. Greater detail concerning the nuclear and biochemical mechanisms responsible for maintaining the nonexpressive viral state, however, is beyond the scope of this review, but can be found in detail elsewhere. Mechanisms of HIV-1 Latency, Bednarik, et al., *AIDS* 6:3–16 (1992).

Until recently, it was believed that HIV was dormant or nonexpressing in all the reservoir population of chronically infected cells during the clinical asymptomatic period. Observations of the low to absent levels of viraemia and virus replication in peripheral blood cells led to the impression that HIV disease was not active during the clinical asymptomatic period. A team of scientists, however, have discovered that a true state of microbiological latency does not exist during the course of HIV infection. Fauci A. S., et al., HIV Infection is Active and Progressive in Lymphoid Tissue During the Clinically Latent Stage of disease, *Nature*, 362:355–358 (1993).

The scientists reported a dichotomy between the levels of viral burden and virus replication in peripheral blood versus lymphoid organs during clinical latency. Based on these findings, therefore, the scientists have discovered that "peripheral blood does not accurately reflect the actual state of HIV disease, particularly early in the clinical course of HIV infection. In fact, HIV disease is active and progressive even when there is little evidence of disease activity by readily measured viral parameters in the peripheral blood, and the patient is experiencing clinical latency."

Inevitably, the disease state of HIV progresses from the clinically latent asymptomatic period to the expressive and active symptomatic period. Through the use of several different models, an understanding of the cellular pathways involved in HIV activation from laboratory latency has begun to unfold. According to Butera, et al., AIDS, 6:994 (1992), many of the cellular models of latency can be induced to express HIV-1 upon treatment with cytokines. This indicates that in the state of microbiologic latency, HIV-1 awaits an extracellular stimulus before initiating replication. This signal not only can be mediated though a soluble cytokine interaction with its receptor, but also through receptor-receptor interactions which occur during cell to cell communication or cellular stress such as UV light exposure and heat shock. Furthermore, an extracellular induction signal can be generated in an autocrine or paracrine fashion so that an HIV-1 activated cell can propagate its own expression while activating a nearby latent cell.

Additional factors have been considered by those of skill in the art to be involved in the activation of HIV. One study has shown that 12-0-tetradecanoylphorbol-13-acetate (TPA) mediates CD4 down regulation and viral expression in HIV-infected cells. Hamamoto, et al., *Biochem, Biophys, Res. Commun.*, 164:339–344 (1989). Interestingly, Hamamoto also examined the effect of the potent protein kinase C inhibitors staurosporine, H-7, and UCN-01 on TPA-mediated CD4 down regulation and augmentation of HIV expression. Staurosporine was found to be an effective TPA inhibitor for both of these actions.

The cellular pathways involved in mediating the activating signal from the plasma membrane to the integrated virus, resulting in HIV-1 expression, are much less clear. Recently, the development of a reliable and simple system for evaluating compounds that could prevent activation of latent HIV was reported at a National Cooperative Discovery Grant (NCDDG)/AIDS meeting by P. Feorino, S. T. Butera, T. M. Folks, and R. F. Schinazi, Nov. 3–7, 1991. The assay system employed the OM-10.1 cell line, a unique chronically-infected promyelocytic clone which remains CD4+ until HIV-1 activation with tumor necrosis factor-α. The expression of CD4+ on the cell surface and the activity of reverse transcriptase are used as markers for quantitating viral expression. Alternatively, other HIV markers, such as protease activity, which are known to those of skill in the art can be used. OM-10.1 cells remain CD4+ until viral activation and respond to tumor necrosis factor induction, and therefore, these cultures are used to conveniently and rapidly examine pharmacologics for an ability to prevent CD4+ down modulation (decrease in expression of CD4+ on the cell surface) and HIV-1 expression.

A variety of compounds known to have antiviral properties against either acutely or chronically infected cells were evaluated for their ability to inhibit HIV expression in these OM-10.1 cells. Several compounds that interact with biochemical pathways that may interfere with the reactivation process were also examined. The results of the evaluation were presented in a poster at the NCDDG/AIDS, San Diego, Calif., November 3-7 (1991). Among some 48 compounds evaluated, 3'-fluoro-3'-deoxythymidine (FLT), interferon Y, and desferrioxamine were considered modest inhibitors of the activation of HIV-1.

A representative compound of Formula I, 2,3-dihydro-9-methoxy-[1]benzothieno [2,3-f]-1,4-thiazepin-5(4H)-one, showed an IC50 of 0.21 µM inhibition in OM-10.1 cells.

In a preferred embodiment of this invention, the compounds of Formula I are utilized to treat and prevent herpesvirus, especially herpes simplex I virus (HSV-1), as well as herpes simplex II virus, and cytomegalovirus. Herpesvirus constitutes a large group of DNA viruses found in many animal species. The nucleic acid is a single molecule of double-stranded DNA and consists of 152,260 base pairs. The viruses mature in the nucleus of the infected cell, where they induce formation of a cytoplasmic inclusion body. Herpesviruses are causative agents of conditions such as oral herpes simplex, genital herpes simplex, varicella, herpes zoster, cytomegalic inclusion disease in humans, and of pseudorabies and other diseases in animals.

Herpesviruses, using HSV-1 as the example, express genes in a temporal sense via transcriptional control. Three distinct groups of HSV-1 gene products are transcribed and translated in a coordinated fashion as a function of the viral life cycle. These groups are described as immediate early, early, or late genes or alternatively by α (alpha), β (beta), or γ (gamma) nomenclature. The immediate early genes, such as ICP4, are first transcribed by host transcription factors and host RNA polymerase II and are required for subsequent transcription of the early and late genes. Herpesvirus genes are generally transcribed from a single promoter for each gene and use cellular RNA II polymerase. The early genes are primarily required for viral DNA synthesis and the late genes for virion structural proteins. Transcription of the three classes of HSV-1 genes requires host cellular transcription factors such as OTF-1 (octamer binding protein). Herpesviruses contain both cis acting DNA sequences and trans acting factors which work in concert with host transcription factors to regulate temporal gene expression. Characteristic of these viral transcription factors is α-TIF (immediate early trans-induction factor, VP16) which interacts with cellular nuclear factors such as OTF-1 and binds at a cis acting DNA sequence to trans activate the transcription of immediate early genes. Many of the same DNA sequence elements found in eukaryotic promoters such as TATA boxes, enhancer like elements, positive and negative regulators, and SP1 binding sites are found in herpesvirus promoter sequences. As such, inhibition of viral transcription by interacting with host cellular proteins complexed with viral encoded transcription factors will prevent herpesvirus replication.

The compounds of Formula I have exhibited excellent activity in standard assays utilized to measure anti-herpesvirus activity. For example, one assay utilized is called the "AVUS" screen.

This screen was designed to identify compounds which inhibit HSV-1 in phases of its life cycle from adsorption and penetration through late gene expression. The primary screen, AVUS1, involves adding single compounds to a monolayer of Vero cells to a final concentration of 25 µg/mL, then infecting the cells with a recombinant HSV-1, Us3::Tn5-lacZ. This virus contains an insertion of a lacZ gene driven by a viral late promoter in the US3 protein kinase gene of HSV-1. The infection is allowed to proceed for 20 hours, then the cells are lysed with a solution of Triton X-100 and CPRG in "Z" buffer and assayed for β-galactosidase activity. The positive control used is solvent alone without compound, which corresponds to 0% inhibition, and the negative control used is either no virus added to the wells or 0.5% Triton X-100 added to the wells, which corresponds to 100% inhibition. Percent inhibition of a compound is then calculated using these positive and negative controls. Those compounds which have a percent inhibition greater than 80% in AVUS1 are carried forward to the secondary screen, AVUS2, in which a titration of the compound from the frozen diluted stock of the AVUS1 screen is assayed for inhibition of HSV-1 via the same β-galactosidase assay and toxicity via a 1-day XTT assay in the absence of virus. Those compounds which have good activities (<2 μg/mL), good therapeutic indices (>10 fold), and which are not planar compounds or are then carried forward to the tertiary screen, AVUS3. In AVUS3, the test compound is dissolved in MeOH at 20 mM. A titration of the compound is then assayed in both the same β-galactosidase virus replication inhibition assay and a 5-day XTT toxicity assay. Follow-up screens to this core set of AVUS screens include plaque reduction and yield reduction assays with wild type HSV-1 to verify antiviral activity, and time course of addition studies to begin to dissect a possible mechanism of action.

The following table shows the anti-herpesvirus activity of 2,3-dihydro-9-methoxy[1]benzothieno[2,3-f]-1,4-thiazepin-5(4H)-one when evaluated according to the foregoing protocol.

| Assay | $IC_{50}$ (μM) | |
|---|---|---|
| | Inhibitory Activity | Toxicity |
| AVUS3 | <0.005 | 60 |
| AVUS3 | <0.0006 | 5 |
| AVUS3 | 0.05 | >>1 |
| AVUS3 | <<0.001 | 7 |
| AVUS3 | 0.03 | 2 |
| AVUS3 | 0.003 | 0.216 |
| AVUS3 | 0.2 | 60 |
| AVUS3 | 0.03 | 4 |
| AVUS3 | 0.01 | |
| AVUS3 | 0.1 | |
| AVUS3 | 0.2 | |
| PRA | 0.45 | |
| PRA | 0.55 | |
| SGC | 0.35 | |

The compounds required to practice the present invention may be prepared by the following methods.

The first general approach requires as starting materials the 3-hydroxy, thiol, or aminobenzo [b]thiophene, benzofuran or indole-2-carboxylate esters of structure 1 (Scheme 1). The 3-hydroxybenzo [b]thiophene-2-esters are prepared as documented [Connor D. T., et al., *J. Med. Chem.,* 35:958 (1992)]. The 3-thio-benzo [b]thiophene -2-carboxylate esters are prepared by treatment of the analogous 3-chloro derivative [Connor D. T., et al., *J. Med. Chem.,* 35:958 (1992)] with thioacetamide in the presence of a base such as 1,8-diaza-bicyclo[5.4.0]-undec-7-ene (DBU) and a solvent such as N,N'-dimethylformamide or tetrahydrofuran. The 3-amino-benzo[b]thiophene-2-carboxylate esters are prepared by the known general method [Beck J. R., *J. Org. Chem.,* 37:3224 (1972)]. The 3-hydroxy-indole-2-carboxylate esters are prepared by known methods such as Unangst P. C., et al., *J. Heterocyclic Chem.,* 24:811 (1987) and Moyer M. P., et al., *J. Org. Chem.,* 51:5106 (1986). The 3-thioindole-2-carboxylate esters are prepared by known methods such as Unangst P. C., et al., *J. Heterocyclic Chem.,* 24:811 (1987); Atkinson J. G., et al., *Synthesis,* 480 (1988); and Nagarajan K., et al. *Indian J. Chem.,* 20B:672 (1981). The 3-amino-indole-2-carboxylate esters are prepared by known methods such as Simakov S. V., et al., *Khim.-Farm. Zu.,* 17:1183 (1983).

The conversion of compounds of type 1 to those of this invention is shown in Scheme 1. The esters are treated with an α-halo-substituted acetonitrile derivative such as bromoacetonitrile in the presence of a base such as potassium t-butoxide in tetrahydrofuran, acetonitrile, or dimethylsulfoxide at 0°–80° C. to provide esters of type 2. The nitrile group is reduced to the corresponding primary amine and the resultant intermediate 3 is cyclized to the lactam 4. The preferred conversion is hydrogenation of 2 with Raney cobalt catalyst in a solvent such as tetrahydrofuran in the presence of a base such as triethylamine at elevated temperature and pressure. Under these conditions 4 is obtained directly from 2. If intermediate 3 is isolated it is cyclized to 4 under basic, preferably NaOMe in methanol, or acidic conditions, preferably polyphosphoric acid, at elevated temperatures.

During the synthesis of some of the invention compounds, it may be necessary or desirable to convert reactive groups such as hydroxy, amino, and carboxy, to derivatives which will protect them from unwanted side reactions when a desired reaction is taking place somewhere else in the molecule. Such protected hydroxy, amino, and carboxy groups are readily deprotected by conventional methods. Commonly used chemical moieties which serve to protect reactive groups such as hydroxy, amino, and carboxy, and methods for their attachment and subsequent removal, are described by Greene and Wuts in *Protective Groups in Organic Synthesis,* John Wiley & Sons, Inc., New York, 1991.

For example, a 3-amino, 3-hydroxy, or 3-thio indole, benzothiophene, or benzofuran (Compound 1 in Scheme 1) can be reacted with a β-halo-ethylenimine where the amino group is protected with a suitable protecting group (PG) such as a t-butoxycarbonyl (Boc) or benzyloxycarbonyl (Cbz). Reaction under the same conditions as described above provides compounds of type 5. Deprotection (i.e., removal of the PG) of 5 under standard conditions, i.e., trifluoroacetic acid or aqueous acid for the removal of the BOC or hydrogenolysis for removal of the Cbz, provides compounds of type 3 that are cyclized as noted earlier. Another approach is the reaction of compounds of type 1 with ethylenimine in an alcoholic solvent to directly provide 3 (see: Nagarajan K., et al. *Indian J. Chem.,* 20B:672 (1981)).

A second general approach (Scheme 2) to compounds of type 4 is from the corresponding 3-halo derivatives 6. Reaction of 6 with ethylenediamine and cupric oxide in a solvent such as pyridine in the presence of a base such as potassium carbonate provides compounds of type 3 where Y is NH (see: Hiremath S. P., et al., *Proc. Nat. Acad. Sci., India,* 60:367 (1990)). Reaction of 6 with cysteamine in a solvent such as dimethylformamide in the presence of a base such as DBU provides compounds of type 3 where Y is S. Reaction of 6 with nitroethanol in a solvent such as tetrahydrofuran in the presence of a base such as potassium t-butoxide or potassium hydride provides compounds of type 7. Subsequent reduction of the nitro group to an amine leads to compounds of type 3 where Y is O. In some of the above cases 3 may not be isolated but 4 may be obtained directly.

A third general approach (Scheme 3) also utilizes the 3-halo derivatives 6. The 3-halo derivative is treated with a primary amine that contains a suitably protected amino, hydroxy or thiol group at the β-position, to forman amide group, providing an intermediate of type 7. Deprotection followed by cyclization leads to compounds of type 4. A similar sequence starts with the 3-hydroxy, thiol or amino compound adding an amine with a suitable leaving group at the β-position. The resultant intermediates of type 8 are then cyclized to give 4.

Those compounds of type 4 where X is S and Y is O or NR can be converted to the corresponding sulfoxide and/or sulfone, 9, with an oxidizing agent such as m-chloroperbenzoic acid (m-CPBA) or an oxaziridine with the reaction conditions determining the extent of oxidation (Scheme 4). For those compounds of type 4 wherein Y is S, similar oxidation would provide either the sulfoxide or sulfone of type 10.

Conditions within the description of Schemes 1 through 4 and variations in the description are known or can readily be determined from analogous reactions known to one skilled in the art.

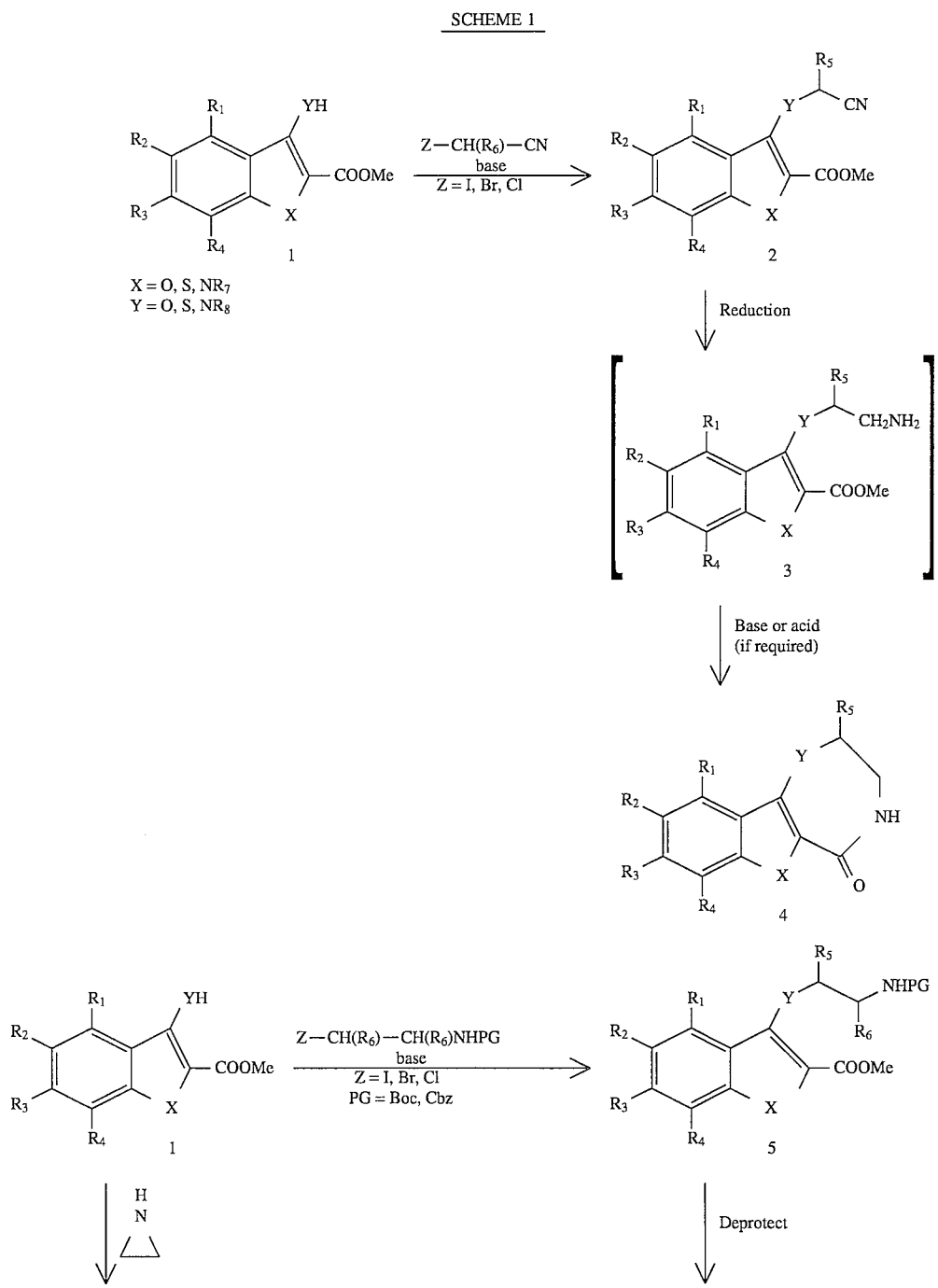

-continued
SCHEME 1
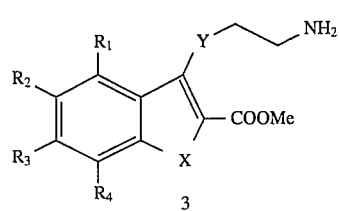
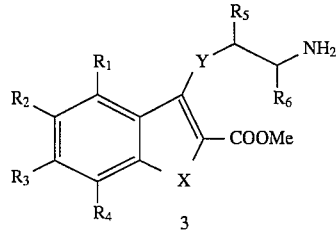
↓ NaOMe/MeOH or PPA
↓ NaOMe/MeOH or PPA
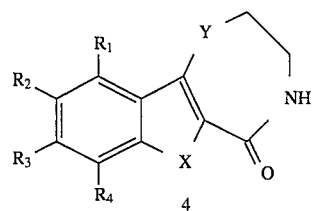
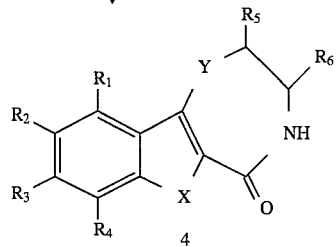
SCHEME 2
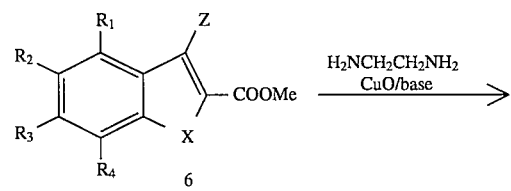
Z = Br, Cl
↓ H₂NCH₂CH₂NH₂ CuO/base
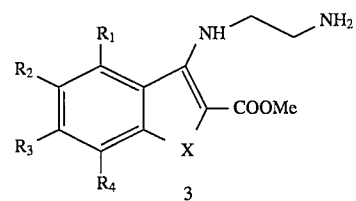
↓ HSCH₂CH₂NH₂ base
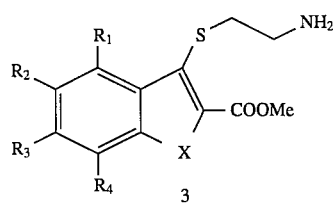
↓ HOCH₂CH₂NO₂ base
-continued
SCHEME 2
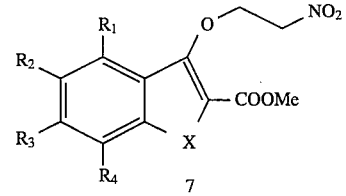
↓ reduction
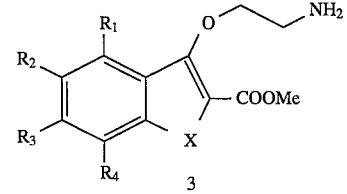
↓ NaOMe/MeOH or PPA
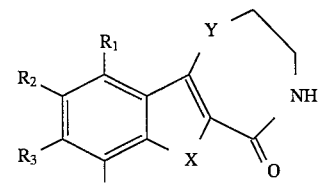

5,612,330
15
SCHEME 3
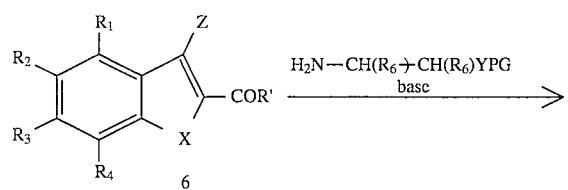
Z = Br, Cl
R' = OH, OMe, Cl
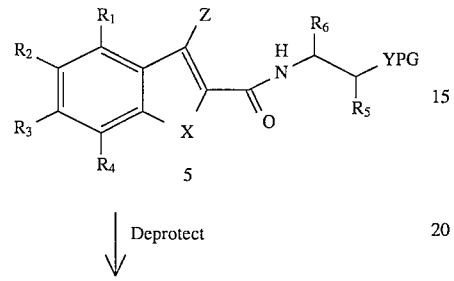
Deprotect
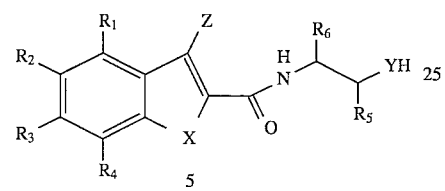
Base
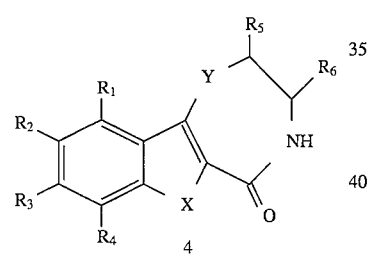
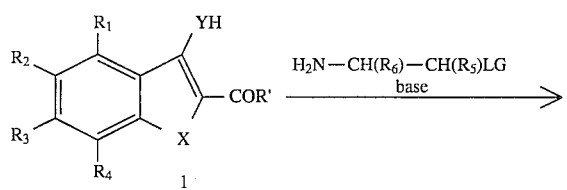
R' = OH, OMe, Cl
16
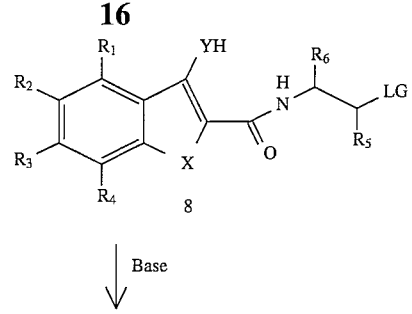
Base
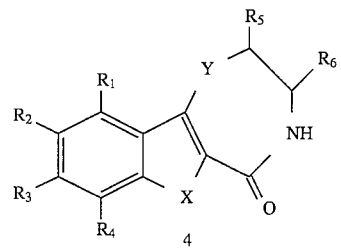
SCHEME 4
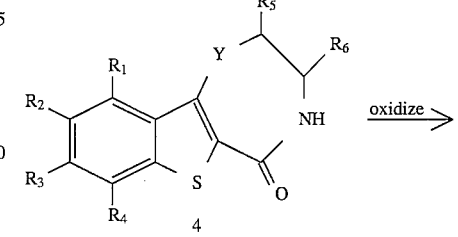
Y = O, NR$_7$
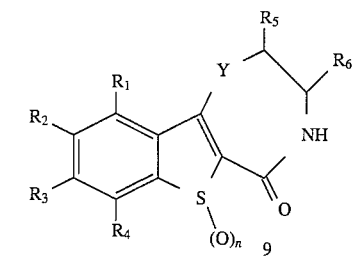
n = 1, 2

17
-continued
SCHEME 4

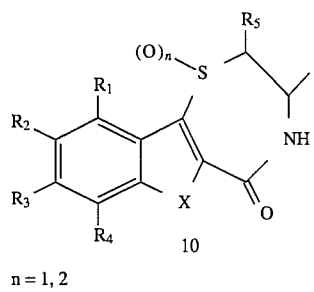

n = 1, 2

The following examples are illustrative of the preparation of the compounds to be utilized in the present invention.

EXAMPLE 1

2,3-Dihydro-9-methoxy[1]benzothieno[2,3-f]-1,4-thiazepin-5(4H)-one

To a room temperature solution of methyl 3-chloromethoxy-benzo[b]thiophene-2-carboxylate (500 mg, 1.95 mmol) [prepared by reaction of the known 3-chloro-5-methoxy-benzo[b]thiophene-2-carbonyl chloride with methanol- [*J. Med. Chem.*, 35:958 (1992)]] in 20 mL of DMF is added cysteamine-HCl (885 mg, 7.79 mmols) followed by DBU (2.33 mL, 15.58 mmol). The reaction mixture is stirred at room temperature for 1.5 hours then warmed to 70° C. The mixture is diluted with ethyl acetate and washed with aqueous HCl, water and brine. The organic layer is dried over MgSO₄, filtered and concentrated in vacuo. The crude product is recrystallized from hexane and ethyl acetate to provide 2,3-dihydro-9-methoxy[1]benzothieno[2,3-f]-1,4-thiazepin-5(4H)-one in 74% yield, mp 209°–209.5° C.

EXAMPLE 2

2,3-Dihydro-[1]benzothieno[2,3-f]-1,4-oxazepin-5(4H)-one

A mixture of the methyl ester of 3-(cyanomethoxy)benzo[b]thiophene-2-carboxylic acid (405 mg, 1.64 mmols) [*J. Hetero. Chem.*, 12:1037 (1975)], 0.5 mL of Et₃N and 0.50 g of RaCo in 50 mL of THF is heated at 100° C. under 1200 psi of hydrogen. The reaction mixture is concentrated in vacuo. Column chromatography eluting with a gradient of 1:1 hexane:ethyl acetate to all ethyl acetate provides 2,3-dihydro-[1]benzothieno[2,3-f]1,4-oxazepin-5 (4H)-one in 55% yield, mp 244°–245° C.

EXAMPLE 3

2,3-Dihydro-9-methoxy-[1]benzothieno[2,3-f]-1,4-thiazepin-5(4H)-one-1-oxide

A mixture of 2,3-dihydro-9-methoxy [1]benzothieno[2,3-f]-1,4-thiazepin-5 (4H)-one (200 mg, 0.75 mmol) and NaBO₃-4H₂O (116 mg, 0.75 mmol) in 18 mL of AcOH is stirred at room temperature overnight. The reaction mixture is filtered and 60 mL of water is added to the filtrate. Filtration provides 2,3-dihydro-9-methoxy-[1]benzothieno[2,3-f]-1,4-thiazepin-5(4H)-one-1-oxide in 69% yield, mp 215°–216° C. (dec).

18

EXAMPLE 4

3,4-Dihydro-9-methoxy-6-methyl-2H-1,4-oxazepino[6,7-b]-indol-5(6H)-one

A. Methyl 3-(cyanomethoxy)-5-methoxy-1-methyl-1H-indole-2-carboxylate

A suspension of potassium tert-butoxide (3.2 g, 29 mmol) in 60 mL of dimethyl sulfoxide is treated in portions with methyl 3-hydroxy-5-methoxy-1-methyl-1H-indole-2-carboxylate (5.6 g, 24 mmol; Unangst P. C., et al., *J. Heterocyclic Chem.*, 24:811 (1987)). The mixture is stirred for 15 minutes, and chloroacetonitrile (4.8 mL, 5.7 g, 76 mmol) is added dropwise. The mixture is heated at 80° for 90 minutes, cooled, and added to 800 g of ice and water. The precipitated solid is filtered, washed with 10% methanol-water, and recrystallized from aqueous acetonitrile to give 3.9 g (60%) of product, mp 136°–137° C.

B. A mixture of methyl 3-(cyanomethoxy)-5-methoxy-1-methyl-1H-indole-2-carboxylate (0.60 g, 2.2 mmol) and triethylamine (0.40 mL, 0.29 g, 2.9 mmol) in 35 mL of tetrahydrofuran in a pressure reaction vessel is treated with Raney cobalt catalyst (0.40 g). The reactor is pressurized with hydrogen (590 psi) and heated at 80° C. for 10 hours. The cooled reaction mixture is filtered and the filtrate evaporated. The oil residue is dissolved in 50 mL of methanol, and sodium methoxide (0.80 g, 15 mmol) is added to the solution. The mixture is heated at reflux for 3 hours, then cooled and evaporated. The residue is distributed between 75 mL of ethyl acetate and 150 mL of brine. The aqueous layer is extracted several times with fresh ethyl acetate. The combined organic layers are washed with brine, dried (anhydrous sodium sulfate) and evaporated. The crude product residue is purified by flash chromatography (silica gel, 5% methanol in dichloromethane elution) to yield 0.18 g (33%) of product. A sample recrystallized from ethyl acetatehexane has mp 184°–186° C.

EXAMPLE 5

2,3-Dihydro-1H-benzothieno-[3,2-e]-1,4-diazepine-5-one, 3-(2-Aminoethylamino)benzo[b]thiophene-2-carboxylic acid methyl ester hydrochloride A solution of 2-(4,5-dihydro-1H-imidazol-2-yl) benzenethiol (1.00 g, 5.62 mmol) [Hegen H., Fleig H. *Justus Liebigs Ann. Chem.* 11:1994 (1975)] and chlormethyl acetate (610 mg, 5.62 mmol) in 15 mL of methanol is heated at reflux for 90 minutes. The reaction is cooled to room temperature and filtered. The filtrate is concentrated to dryness and the residue dissolved in hot chloroform. After several hours the resulting precipitate is collected and dried. The mother liquor affords a second crop of crystals giving 3-(2-aminoethylamino)benzo[b]thiophene-2-carboxylic acid methyl ester hydrochloride in an overall yield of 61%, mp 219°–220° C.

2,3-Dihydro-1H-benzothieno-[3,2-e]-1,4-diazepin-5-one

A solution of 3-(2-aminoethylamino)benzo[b]thiophene-2-carboxylic acid methyl ester hydrochloride (339 mg, 1.18 mmol) and freshly prepared sodium methoxide (from 134 mg, 2.48 mmol of sodium) in 5 mL of methanol is heated at reflux for 18 hours. Upon cooling, the reaction is neutralized with 25 mL of 1N HCl and cooled to 0° C. for 1 hour. The resulting yellow crystalline material is filtered and dried under vacuum at 60° C. for several hours to provide 2,3-dihydro-1H-benzothieno [3,2-e]-1,4-diazepin-5-one in 64% yield. Chromatography, eluting with a gradient of 2% methanol in ethyl acetate in 5% methanol in ethyl acetate, gives analytically pure, 2,3-dihydro-1H-benzothieno-[3,2-e]-1,4-diazepin-5-one, mp 210°–212° C.

EXAMPLE 6

2,3-Dihydro-9-methoxy-1H-benzothieno-[2,3-f]-1,4-oxazepin-5-one

3-Cyanomethoxy-5-methoxy-benzo[b]thiophene-2-carboxylic acid methyl ester

To a room temperature solution of methyl 3-hydroxy-5-methoxybenzo[b]thiophene-2-carboxylate (1.00 g, 4.2 mmol) [Connor, et al., *J. Med. Chem.* 35:959 (1992)]in 20 mL of DMSO is added potassium t-butoxide (494 mg, 4.41 mmol) followed by bromoacetonitrile (878 µL, 12.58 mmol). The mixture is stirred at room temperature for 1.5 hours, then poured into ethyl acetate and 1N HCl. The organic layer is washed with 1N HCl, followed by several portions of brine, and dried over $MgSO_4$. Filtration followed by removal of solvent in vacuo and recrystallization of the residue from ethyl acetate:hexane gives 413 mg. An additional crop of 112 mg can be obtained from the mother liquor, mp 159.5°–160° C.

2,3-Dihydro-9-methoxy-1H-benzothieno-[2,3-f]-1,4-oxazepin-5-one

A solution of 3-cyanomethoxy-5-methoxy-benzo[b]-thiophene-2-carboxylic acid methyl ester (2.5 g, 9.0 mmol) in 50 mL of THF is heated to vigorous reflux. Borane-dimethyl sulfide (9.0 mL, 90.2 mmol) is rapidly added and heating continued for 25 minutes with THF being added as it evaporates. An additional amount of borane-dimethyl sulfide (4.0 mL) is added and heating continued for 10 minutes. The reaction mixture is cooled to 0° C. and 50 mL of 6N HCl is carefully added. Hydrogen gas is evolved and the temperature of the reaction mixture increases. The resultant precipitate is collected by filtration, washed with water, and dried in vacuo overnight.

The solid (2.3 g, 8.2 mmol) is added to a freshly prepared solution of sodium methoxide (from 1.9 g, 82.0 mmol of sodium) in 40 mL of methanol. The reaction mixture is warmed to 50° C. for 2 hours, then heated at reflux for 2 hours. After cooling to room temperature, the precipitate is collected and washed with cold methanol, followed by cold diethyl ether. The solid is dried in vacuo overnight to give 1.18 g (52%). An analytical sample of 2,3-dihydro-9-methoxy-1H-benzothieno-[2,3-f]-1,4-oxazepin-5-one is obtained by recrystallization from ethyl acetate:hexane, mp 264°–265° C.

EXAMPLE 7

2,3-Dihydro-9-methoxy-6-oxide-1H-benzothieno-[2,3-f]-1,4-oxazepin-5-one

To a suspension of 2,3-dihydro-9-methoxy-1H-benzothieno-[2,3-f]-1,4-oxazepin-5-one (1.00 g, 4.0 mmol) in 100 mL of warm methanol is added 30% hydrogen peroxide (8.0 mL, 80 mmol) followed by selenium dioxide (445 mg, 4.01 mmol). The reaction mixture is stirred at room temperature for 3 hours then heated at 30° C. for 1.5 hours followed by heating at 40° C. for 2 hours. The reaction mixture is cooled to −40° C. and the resulting precipitate is collected by filtration. The residue is chromatographed eluting initially with 5% methanol in ethyl acetate gradually increasing the solvent polarity to 1:1 methanol:ethyl acetate to give 338 mg of product. An analytical sample of 2,3-dihydro-9-methoxy-6-oxide-1H-benzothieno [2,3-f]-1,4-oxazepin-5-one is obtained by recrystallization from methol:ethyl acetate, mp 273°–274° C.

EXAMPLE 8

2,3-Dihydro-9-methoxy-2-methyl-1H-benzothieno-[2,3-f]-1,4-oxazepin-5-one 3-(1-Cyanoethoxy)-5-methoxy-benzo[b]thiophene-2-carboxylic acid methyl ester To a room temperature solution of methyl 3-hydroxy-5-methoxybenzo[b]thiophene-2-carboxylate (1.00 g, 4.2 mmol) [Connor, et al., *J. Med. Chem.*, 35:958 (1992)]in 20 mL of DMSO is added potassium t-butoxide (494 mg, 4.41 mmol) followed by 2-chloropropionitrile (1.1 mL, 12.6 mmol). The mixture is stirred at room temperature for 1.5 hours then warmed to 82° C. for 3 hours. The reaction mixture is poured into ethyl acetate and 1N HCl. The organic layer is washed with 1N HCl, followed by several portions of brine and dried over $MgSO_4$. Filtration followed by removal of solvent in vacuo and recrystallization of the residue from ethyl acetate:hexane gives 853 mg, mp 127°–129° C.

2,3-Dihydro-9-methoxy-2-methyl-1H-benzothieno-[203-f]-1,4-oxazepin-5-one

A solution of 3-(1-cyanoethoxy)-5-methoxybenzo[b]-thiophene-2-carboxylic acid methyl ester (400 mg, 1.37 mmol) in 10 mL of THF is heated to vigorous reflux. Borane-dimethyl sulfide (1.4 mL, 13.7 mmol) is added dropwise and heating continued for 20 minutes with THF being added as it evaporates. The reaction mixture is cooled to room temperature and 7.5 mL of 6N HCl is carefully added. After 5 minutes the reaction mixture is cooled to 0° C. and 68.5 mL of 1N NaOH is added followed by ethyl acetate. The layers are separated and the organic phase is washed with 1:1 brine:water, then with additional brine. The organic phase is dried over $MgSO_4$, filtered, and concentrated in vacuo. The residue is chromatographed eluting with a gradient of 5:25:70 methanol:hexane:chloroform to 10:90 methanol:chloroform to 30:70 methanol:chloroform to give 135 mg of product. An analytical sample of 2,3-dihydro-9-methoxy-2-methyl-1H-benzothieno-[2,3-f]-1,4-oxazepin-5-one is obtained by recrystallization from ethyl acetate:hexane, mp 185°–186° C.

The invention compounds are readily formulated with common diluents and carriers for convenient oral, topical or parenteral administration to humans and animals for treatment of diseases of viral origin, for example, cold sores caused by herpes simplex virus I, as well as HIV and AIDS caused by HIV. The following examples illustrate the preparation of typical pharmaceutical formulations.

EXAMPLE 9

Preparation of 250-mg Capsule 2,3-Dihydro-9-isopropoxy-7-chloro-1H-benzothieno-[2,3-f]-1,4-oxazepin-5-one (250 mg), is blended to uniformity with 150 mg of lactose and 150 mg of corn starch. The mixture is encapsulated into gelatin capsules. Such capsules are orally administered at the rate of one to three each day for treatment of cold sores.

EXAMPLE 10

Formulation for Oral Suspension

| Ingredient | Amount |
| --- | --- |
| 2,3-Dihydro-8-ethyl-10-trifluoro-methyl-6-oxide-1H-benzothieno-[2,3-f]-1,4-oxazepin-5-one | 500 mg |
| Sorbitol solution (70% N.F.) | 40 mL |
| Sodium benzoate | 150 mg |
| Saccharin | 10 mg |
| Cherry Flavor | 50 mg |
| Distilled Water q.s. ad. | 100 mL |

The sorbitol solution is added to 40 mL of distilled water and the oxazepinone is suspended thereon. The saccharin, sodium benzoate, and flavoring are added and dissolved. The volume is adjusted to mL with distilled water. Each milliliter of syrup contains 5 mg of the oxazepinone. This oral formulation is ideally suited for treating herpesvirus infections in pediatric care.

EXAMPLE 11

Preparation of Parenteral Solutions

In a solution of 700 mL of propylene glycol and mL of distilled water for injection is dissolved 20.0 g of 2,3-dihydro-7-dimethylamino-1H-benzothieno-[3,2-e]-1,4-diazepin-5-one. The pH of the solution is adjusted to 5.5 with hydrochloric acid, and the volume is made up to 1000 mL with distilled water. The formulation is sterilized, filled into 5.0 mL ampoules each containing 2.0 mL (representing 40 mg of active diazepinone) and sealed under nitrogen. The formulation is administered intravenously to patients suffering from Herpesvirus, HIV, or AIDS.

EXAMPLE 12

Preparation of Topical Cream

Five hundred milligrams of 2,3-dihydro-7-ethoxybenzofurano-[2,3-f]-1,4-oxazepin-5-one is mixed with 15 g of cetyl alcohol, 1 g of sodium lauryl sulfate, 40 g of liquid silicone D.C. 200 (sold by Dow Corning Co., Midland, Mich.), 43 g of sterile water, 0.25 g of methylparaben, and 0.15 g of propylparaben. The mixture is warmed to about 75° C. with constant stirring, and then cooled to room temperature at which it congeals. The preparation is applied to the skin surface of a person suffering from herpesvirus, for instance, cold sores caused by herpes simplex I, shingles caused by herpes zoster, and the like.

We claim:

1. A method of inhibiting treating herpesvirus comprising administering to a subject in need of treatment an anti-herpesvirus amount of a compound of the formula

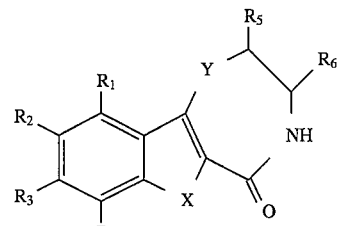

or a pharmaceutically acceptable acid addition salt thereof, wherein $R_1$, $R_2$, $R_3$, and $R_4$ are each independently hydrogen, hydroxy, halogen, lower alkyl, lower alkoxy, benzyloxy, trifluoromethyl, nitro, or —$NR_8R_9$, in which $R_8$ and $R_9$ are each independently hydrogen or lower alkyl;

$R_5$ and $R_6$ are each independently hydrogen, lower alkyl or phenyl;

X is O, $S(O)_n$ or $NR_7$;

Y is O, $S(O)_n$ or $NR_8$;

$R_7$ is hydrogen, lower alkyl, phenyl, benzyl, $CH_2OR_8$ or lower alkyl, phenyl, benzyl substituted with halo;

$R_8$ is hydrogen, lower alkyl or phenyl;

n is an integer of 0, 1 or 2;

with the provisos that
1) when X is NH, Y is NH, $R_1$ is H, $R_3$ is H and $R_4$ is Br, $R_2$ is not methyl;
2) when X is NH, Y is NH, $R_1$, $R_3$ and $R_4$ are H, $R_2$ is not methoxy or ethoxy; and
3) when X is NH, Y is S, at least one of $R_1$, $R_2$, $R_3$, and $R_4$ is not H.

2. A method of claim 1 employing a compound wherein $R_1$, $R_3$, and $R_4$ are hydrogen.

3. A method of claim 2 wherein $R_2$ is hydrogen or lower alkoxy; X is O, $S(O)_n$ or $NR_7$; Y is O or $S(O)_n$; $R_7$ is hydrogen or lower alkyl, and n is 1 or 2.

4. A method of claim 3 employing 2,3-dihydro-9-methoxy-[1]benzothieno[2,3-f]-1,4-thiazepin-5(4H)-one.

5. A method of claim 3 employing 2,3-dihydro-[1]benzothieno-[2,3-f]-1,4-oxazepin-5 (4H)-one.

6. A method of claim 3 employing 2,3-dihydro-9-methoxy-[1]benzothieno[2,3-f]-1,4-thiazepin-5(4H)-one-1-oxide.

7. A method of claim 3 employing 3,4-dihydro-9-methoxy-6-methyl-2H-1,4-oxazepino[6,7-b]-indol-5(6H)-one.

8. A method of claim 3 employing 2,3-dihydro-1H-benzothieno-[3,2-e]-1,4-diazepine-5-one.

9. A method of claim 3 employing 2,3-dihydro-9-methoxy-1H-benzothieno-[2,3-f]-1,4-oxazepin-5-one.

10. A method of claim 3 employing 2,3-dihydro-9-methoxy-6-oxide-1H-benzothieno-[2,3-f]-1,4-oxazepin-5-one.

11. A method of claim 3 employing 2,3-dihydro-9-methoxy-2-methyl-1H-benzothieno-[2,3-f]-1,4-oxazepin-5-one.

* * * * *